(12) United States Patent
Deaton, Jr. et al.

(10) Patent No.: US 7,906,746 B2
(45) Date of Patent: Mar. 15, 2011

(54) LASER SHOCK PEENING SYSTEM WITH TIME-OF-FLIGHT MONITORING

(75) Inventors: John Broddus Deaton, Jr., Niskayuna, NY (US); Farzin Homayoun Azad, Clifton Park, NY (US); Magdi Naim Azer, Niskayuna, NY (US); Todd Jay Rockstroh, Maineville, OH (US)

(73) Assignee: General Electric Company, Niskayuna, NY (US)

( * ) Notice: Subject to any disclaimer, the term of this patent is extended or adjusted under 35 U.S.C. 154(b) by 1052 days.

(21) Appl. No.: 11/164,650

(22) Filed: Nov. 30, 2005

(65) Prior Publication Data
US 2007/0119824 A1    May 31, 2007

(51) Int. Cl.
*B23K 26/00* (2006.01)
*B23K 20/04* (2006.01)

(52) U.S. Cl. ...................... 219/121.85; 219/62

(58) Field of Classification Search ... 219/121.6–121.86
See application file for complete search history.

(56) References Cited

U.S. PATENT DOCUMENTS

| | | | |
|---|---|---|---|
| 4,210,028 A * | 7/1980 | Hildebrand | 73/598 |
| 4,504,727 A * | 3/1985 | Melcher et al. | 219/121.62 |
| 5,591,009 A | 1/1997 | Mannava et al. | |
| 5,620,307 A | 4/1997 | Mannava et al. | |
| 5,674,328 A | 10/1997 | Mannava et al. | |
| 5,674,329 A | 10/1997 | Mannava et al. | |
| 5,675,892 A | 10/1997 | Mannava et al. | |
| 5,948,293 A | 9/1999 | Somers et al. | |
| 5,951,790 A | 9/1999 | Mannava et al. | |
| 5,974,889 A | 11/1999 | Trantow | |
| 5,987,991 A | 11/1999 | Trantow et al. | |
| 6,075,593 A | 6/2000 | Trantow et al. | |
| 6,191,385 B1 | 2/2001 | O'Loughlin et al. | |
| 6,254,703 B1 | 7/2001 | Sokol et al. | |
| 6,483,578 B1 | 11/2002 | Clauer et al. | |
| 6,512,584 B1 | 1/2003 | O'Loughlin et al. | |
| 6,539,773 B2 | 4/2003 | Clauer et al. | |
| 6,554,921 B2 | 4/2003 | Sokol et al. | |
| 6,629,464 B2 | 10/2003 | Suh et al. | |

(Continued)

FOREIGN PATENT DOCUMENTS
EP    1528110    5/2005

OTHER PUBLICATIONS

J.P. Chen et al., "Instantaneous Measurements of Laser-Induced Plasma Shock Waves With an Optical Fiber Sensor," Optics Communications, North-Holland Publishing Co., Amsterdam, NL, vol. 168, No. 5-6, Sep. 15, 1999, pp. 343-347.

(Continued)

*Primary Examiner* — Sang Y Paik
(74) *Attorney, Agent, or Firm* — Francis T. Coppa

(57) ABSTRACT

A system and method for monitoring a laser shock peening process includes a sensor connected to a controller. The controller includes an input and a processor. The input is connected to the sensor to receive a signal indicative of a laser shock event at a workpiece. The processor is connected to the input and is configured to determine a time-of-flight of residual energy associated with the laser shock event from the workpiece to the sensor and determine peen quality from the time-of-flight of the residual energy.

20 Claims, 3 Drawing Sheets

U.S. PATENT DOCUMENTS

| | | | |
|---|---|---|---|
| 6,914,215 | B2 | 7/2005 | Davis et al. |
| 7,148,448 | B2 * | 12/2006 | Warren et al. ............ 219/121.83 |
| 2003/0062349 | A1 | 4/2003 | Suh et al. |
| 2004/0262276 | A1 | 12/2004 | Davis et al. |
| 2007/0134721 | A1 * | 6/2007 | Laitenberger et al. ......... 435/7.1 |

OTHER PUBLICATIONS

EP 06125146, EP Search Report, May 2, 2007.

J.P. Chen, X.W Ni, J. Lu, B.M Bian; "Instantaneous measurements of laser-induced plasma shock waves with an optical fiber sensor"; Optics Communications, North-Holland Publishing Co., Amsterdam, NL; vol. 168, No. 5-6, Sep. 15, 1999, pp. 343-347.

CN Office Action, Oct. 16, 2009.

EP Search Report, Sep. 5, 2007.

EP Office Action, Jan. 2, 2008.

* cited by examiner ial stress in the outer layer of the processed part being processed. Still other
LASER SHOCK PEENING SYSTEM WITH TIME-OF-FLIGHT MONITORING

BACKGROUND OF THE INVENTION

The present invention relates generally to laser shock peening and, more particularly, relates to a system and method for monitoring the shock peening process through monitoring of a time-of-flight of the shock wave.

Laser shock peening or laser shock processing (LSP), is a process whereby a shockwave is impinged upon a surface of a part and produces a region of compressive residual stress in an outer layer of the part. It is well understood that the compressive residual stress in the outer layer of the processed part increases the service life of a processed part with respect to cyclic fatigue failure. Understandably, the ability of the part to withstand fatigue failure is dependent, in part, on the quality of the coupling of the shockwave with the part. That is, if the shockwave is not appropriately coupled at the surface of the part, the quality of the peen of the resultant peening process is detrimentally affected.

During the laser shock peening process, a laser generator creates a laser beam that is directed toward the part to be processed. Preferably, to improve the coupling of the energy of the laser beam with the part being processed, an absorption layer and a containment layer are positioned between the part and the laser generator. Generally, the absorption layer and the containment layer are positioned adjacent the part. The laser beam is allowed to pass through the containment layer, usually water, and impinge upon the absorption layer. The absorption layer is generally formed of a thin coating of tape, paint, ink, or foil and is commonly applied directly to the part being processed or maintained in very close proximity thereto. The containment layer is generally located adjacent the absorption layer between the absorption layer and the laser generator. The interaction of the laser beam with the absorption layer produces ablation of the absorption layer, which ultimately generates a shockwave that expands from the absorption layer/confinement layer interface. The containment layer ensures that a substantial portion of the initial shockwave is directed toward the part being processed and thereby enhances the coupling of the shockwave generated by the energy of the laser with the part.

Current practice of laser shock peening requires extensive destructive testing to ensure that parts being processed achieve a desired processing effect. That is, when several parts are to be processed, a select few of the total number of processed parts will be tested to failure to ensure the quality of the remainder of the parts. This type of destructive testing is often time consuming and expensive to implement and execute. Additionally, such testing provides no indication of a real-time, individual peen quality of the part being processed. The failure tested parts are fully processed prior to any testing. The processing of subsequent parts must then be suspended to allow time to failure test the part or continue with the potential of producing parts which do not satisfy quality criteria. Suspending the processing procedure and/or producing subsequent parts which do not satisfy quality criteria detrimentally affects overall process efficiency.

Other systems and processes attempt to improve the process efficiency through real-time sample part processing. That is, these systems process a much smaller part or coupon and determine the quality of the coupling through testing of the coupon. While these approaches improve the real-time aspect of quality control, they must also associate the quality of the test coupon coupling with coupling of an actual part being processed. Such testing can result in misleading data characterizations and associations when the data acquired is not associated with an actual part being processed. Still other systems non-destructively test the quality of the coupling through measurements of characteristics of a processed part such as surface hardness values and peen depth and shape data. Such approaches are incapable of accounting for real-time variations in the coupling quality and analyze only a very few of the many peen sites. Yet other systems monitor parameters and data acquired during processing of a part, destructively test a select group of parts, and compare the extensive data acquired during processing with the data of the destructively tested parts. Although this approach allows for a quality comparison of each part of a group of processed parts, the process still requires the destructive testing of a select group of parts to acquire the control quality data.

Therefore, it would be desirable to design a laser shock peening system and method capable of real-time non-destructive quality monitoring of the peening process.

BRIEF DESCRIPTION OF THE INVENTION

The present invention provides a system and method capable of real-time monitoring of the laser shock peening process that solves the aforementioned problems. The system includes a laser generator configured to direct a laser beam toward a part to be processed. A controller is connected to a laser generator and controls the operation thereof. A sensor is connected to the controller and is configured to detect generation of the laser shock event proximate a workpiece. The controller determines the flight time from the workpiece to the sensor of the residual energy attributable to the laser shock event and determines a peen quality from the time-of-flight of residual energy.

Therefore, in accordance with one aspect of the present invention, a controller includes an input and a processor. The input is configured to receive a signal from a transducer that is indicative of a laser shock event at a workpiece. The processor is connected to the input and is configured to determine a travel time of energy associated with the laser shock event from the workpiece to the transducer and output a determination of peen quality from the travel time.

According to another aspect of the present invention, a laser shock peening system includes a laser source, a sensor, and a controller. The laser source is constructed to emit a laser beam at a workpiece and the sensor is directed toward the workpiece to detect generation of a shock event thereat. The controller is connected to the laser source and the sensor, and is configured to receive a first signal from the laser source and a second signal from the sensor, determine a time-of-flight value from the first signal and the second signal, and determine a quality of a peen from the time-of-flight value.

In accordance with a further aspect of the present invention, a method of monitoring a laser shock peening process is disclosed that includes detecting emission of a laser beam from a laser source towards a workpiece for initiation of a peen event, detecting a residual energy associated with generation of a shockwave generated by impingement of the laser beam on an absorption layer, and determining a time duration between generation of the residual energy and detection of the residual energy. Peen quality is then derived from the determined time duration.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Figure 1:
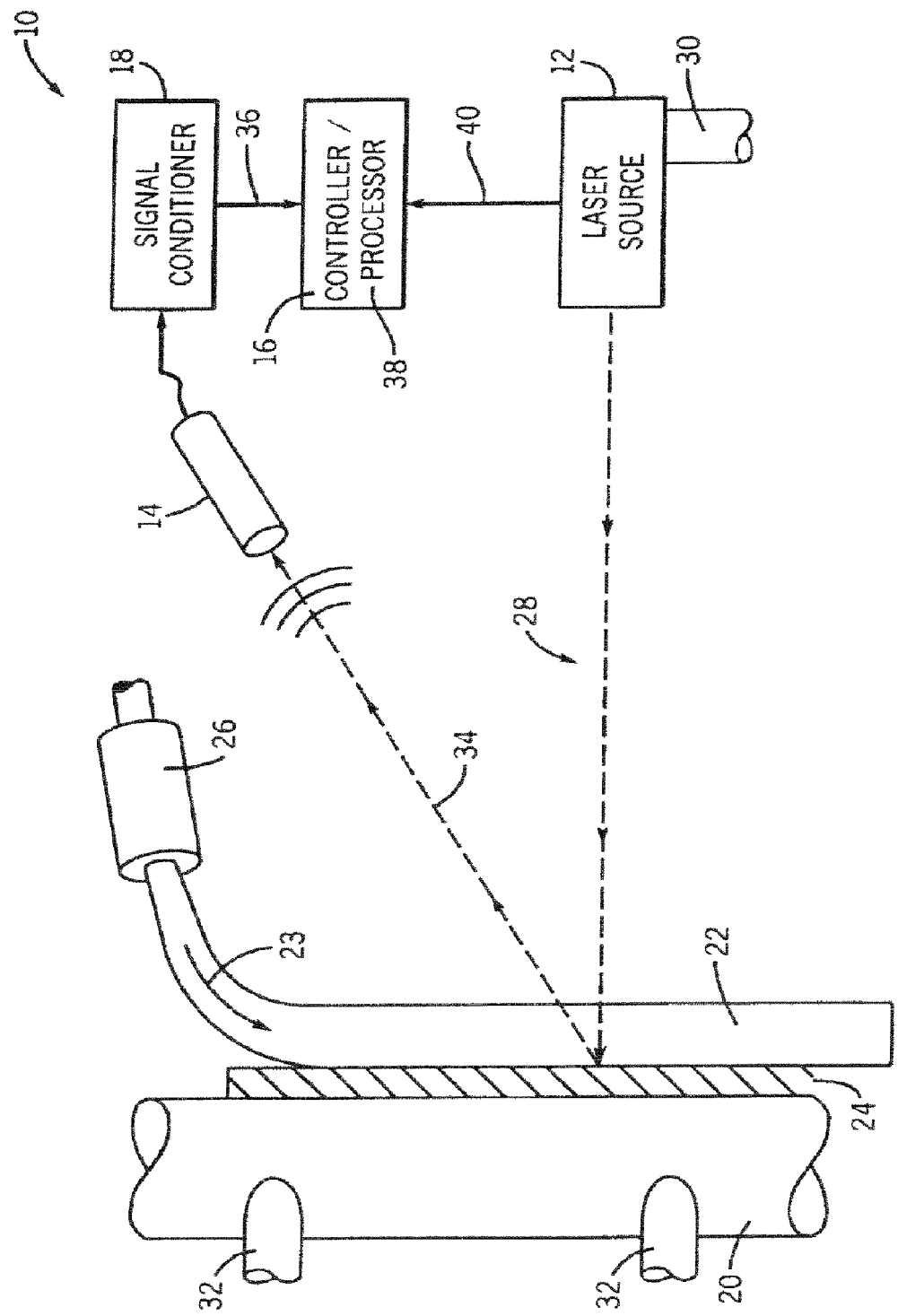
FIG. 1 is a laser peening system according to the present invention.

FIG. 1 shows a laser shock peening system 10 according to the present invention. System 10 includes a laser source 12 and a sensor 14, such as an airborne acoustic signal sensor, connected to a controller 16. Laser source 12 is preferably a high peak power Q-switched laser source; however, other laser sources may be utilized with the content of the present invention. A signal conditioner 18 is disposed between sensor 14 and controller 16 and is configured to receive an input signal from sensor 14 and deliver a modified output signal, preferably an amplified output signal, to controller 16.

Laser source 12 and sensor 14 are directed toward a workpiece 20, such as a fan, compressor, or turbine part or any part intended to be laser shock processed. A containment layer 22 and an absorption layer 24 are maintained in relatively close proximity to workpiece 20. Containment layer 22 is preferably a stream of water, indicated by arrow 23, which is directed at workpiece 20 by a nozzle 26 such that a relatively thin layer of water is maintained between laser source 12 and absorption layer 24. Absorption layer 24, preferably a thin paint, tape, ink, or foil coating, is maintained between containment layer 22 and workpiece 20.

During operation of system 10, laser source 12 emits a laser beam, indicated by arrow 28, directed at workpiece 20. Preferably, laser beam 28 has an energy signal of 1-50 Joules at a pulse duration of approximately 20 nanoseconds. Understandably, other laser beam energy signals are envisioned and applicable with the present invention as may be required to achieve a desired peen from the laser shock process. Laser source 12 is attached to a laser fixture 30 and workpiece 20 is attached to a workpiece fixture 32. Manipulation of fixtures 30, 32, generally by robotic control, allows precise movement of laser source 12 and workpiece 20 such that laser beam 28 is precisely impinged upon absorption layer 24.

When a peen is desired, laser beam 28 passes through containment layer 22 and is impinged on absorption layer 24. Impingement of laser beam 28 on absorption layer 24 generates a shock wave (not shown) which propagates substantially radially outward from the site of impingement of laser beam 28 on absorption layer 24. Containment layer 22 redirects a portion of the shock wave initially directed away from workpiece 20 back toward workpiece 20. Such containment improves the coupling of the energy of laser beam 28 with workpiece 20. Efficient coupling of the energy of laser beam 28 with workpiece 20 ensures that a majority of the energy of laser beam 28 is utilized for the peen processing of workpiece 20.

Once the site associated with the impingement of laser beam 28 has been peen processed, a portion of residual energy, indicated by arrow 34, radiates away from workpiece 20. Sensor 14 is positioned relative to workpiece 20 to detect residual energy 34. Understandably, sensor 14 could be configured to detect any of a variety of types of residual energy including sound/shock waves and/or light signals. Preferably, sensor 14 is configured to monitor the airborne acoustic signal associated with residual energy 34. Sensor 14 communicates electrical signals representing the detection of residual energy 34 to a first input, indicated by arrow 36, of controller 16 through signal conditioner 18.

Figure 2:
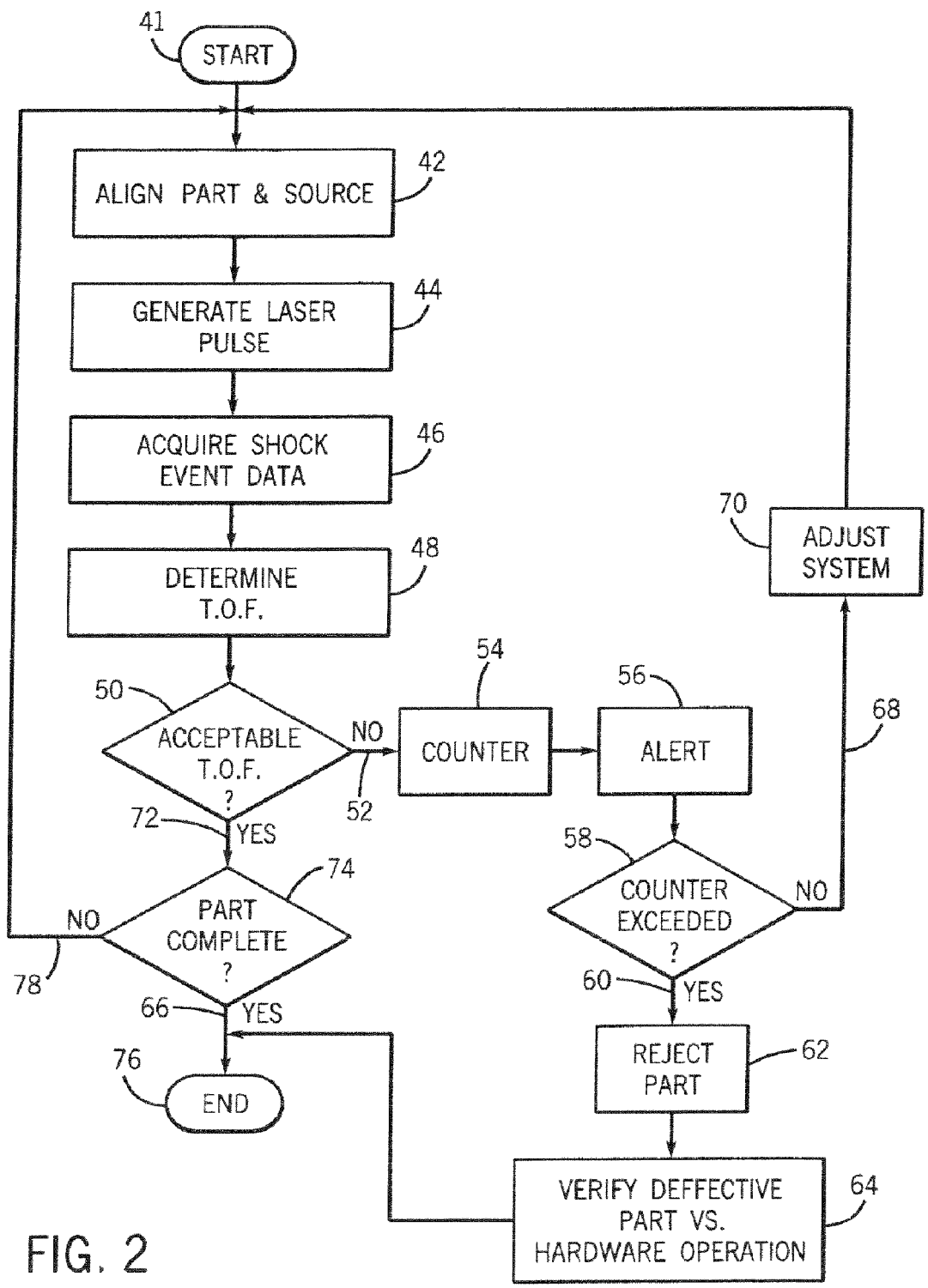
FIG. 2 shows a control process of the laser peening system of FIG. 1.

Controller 16 includes a processor 38 which receives first input 36 from sensor 14 and a second input, indicated by arrow 40, from laser source 12. As shown in FIG. 2, upon initialization 41 of system 10, the workpiece and laser source are aligned 42 such that the laser beam generated by the laser source impinges the workpiece at a desired peen site. A laser pulse is generated 44 which impinges on the workpiece and produces a shock wave and the residual energy associated therewith. The processor acquires shock event data 46 related to the particular peen and then determines a time-of-flight (T.O.F.) required for the residual energy to travel from the workpiece to the sensor. A given time-of-flight value is calculated from the values of the distance of the laser source from the workpiece, the distance of the sensor from the workpiece, and the energy of the laser beam generated by the laser source as derived from the first and second signals.

A brief description of the theory behind the present invention will now be described. The velocity of the shockwave associated with the residual energy is much higher than the ambient sound wave velocity of air relatively close to the point of laser incidence with the workpiece. Furthermore, the higher the initial energy level of the laser source, the greater the difference between the initial shock wave velocity attributable to the peen event and the ambient sound wave velocity for air. Accordingly, the travel time of the shockwave attributable to the peen event, from the workpiece to the sensor at a known location, will decrease as energy imparted to the peening process increases. The energy imparted to the peening process, or utilized to generate the plasma necessary for generation of the peen producing shock wave, provides an indication of the how well the laser shock process is performing. Determining the time-of-flight of the residual energy shockwave provides a real-time indication of the laser shock process and the quality of a peen resulting therefrom. As will be further discussed with respect to FIG. 3, the time-of-flight of the residual energy wave provides an indication of the quality of the coupling of the laser energy with the part and can be used to determine the quality of individual peens during real-time processing of a part.

Referring back to FIG. 2, the determined time-of-flight 48 is compared to a desired time-of-flight data specific to a given system at 50 to determine if the time-of flight is acceptable. That is, acceptable time-of-flight values will be determined based on the physical configuration of the peening system including the power provided by the laser source, distances between the laser source and the workpiece, and the distance between the workpiece the sensor. For a given system then, the comparison made at 49 is to a fixed value or minimally to a range of time-of-flight values.

If an unacceptable time-of-flight 52 is determined, an optional counter 54 is initiated to count the number of occurrences of unacceptable time-of-flight data. In addition to counting the number of occurrences of unacceptable time-of-flight events, an optional alert 56 can be provided to allow an opportunity to address correctable causes of the unacceptable time-of-flight events. If the part has exceeded a maximum number of unacceptable time-of-flight events 58, 60, which indicates that the part has exceeded a tolerable standard for unacceptable peen events, the part is rejected 62. After rejection of a part, an operator is allowed to verify that the cause of the rejection is extraneous to the peening process, such as a part defect, or correct the hardware configuration/operation, such as the fixturing of the parts/components, to prevent subsequent unsuccessful processing 64. Once the part has been rejected 62 it is also categorized as complete 66 thereby preventing further processing of an already unacceptable part.

If an unacceptable time-of-flight 52 is derived, and the counter has not exceeded a maximum count 58, 68, a system adjustment 70 is provided to attempt to avoid repetition of an unacceptable time-of-flight event. System adjustment can include, for example, adjustment of the laser emission energy, alignment of the part with the laser source, and/or containment layer direction and thickness. Regardless of the laser energy parameter or the peen event parameter that is adjusted, the automatic adjustment of the parameter allows the peening process to continue upon automatic correction of the possible cause of the unacceptable peen event.

Upon clearing the system adjustment 70, the part and laser source are realigned 42 for processing of a subsequent peen site. If the derived time-of-flight is acceptable 50, 72, a part completion 74 is checked to verify that a part has been subjected to a desired number of peen events. If the part has been subjected to a desired number of peen events 74, 66, and count 58 has not been exceeded 68, the quality of the part is acceptable and the processing of the part is complete 76. If the part has not been subjected to a desired number of peen events 74, 78, the part and the laser source are realigned for subsequent peen events until processing of the part is complete 66. Such a system provides a repeatable, on-the-go, real-time monitoring, adjusting, and processing of a laser peening process and the part associated therewith, respectively. Additionally, by monitoring the time-of-flight of the residual energy of the laser shock event, the sensor and controls thereof can be located somewhat remote from the site of the laser shock event. Sensor 14 is positioned approximately 50 mm from the laser shock site and is preferably positioned at least 30 mm from the laser shock site. Such an orientation reduces the stresses that the sensor is subjected to due to the proximity of the sensor to the laser shock event. Additionally, as the time-of-flight value can be determined essentially independent of set-off distances of the sensor relative to the workpiece and the orientation of the sensor relative to the laser shock site, determining peen quality as a function of time-of-flight of the residual energy can be quickly and efficiently adapted to a specific production environment.

Figure 3:
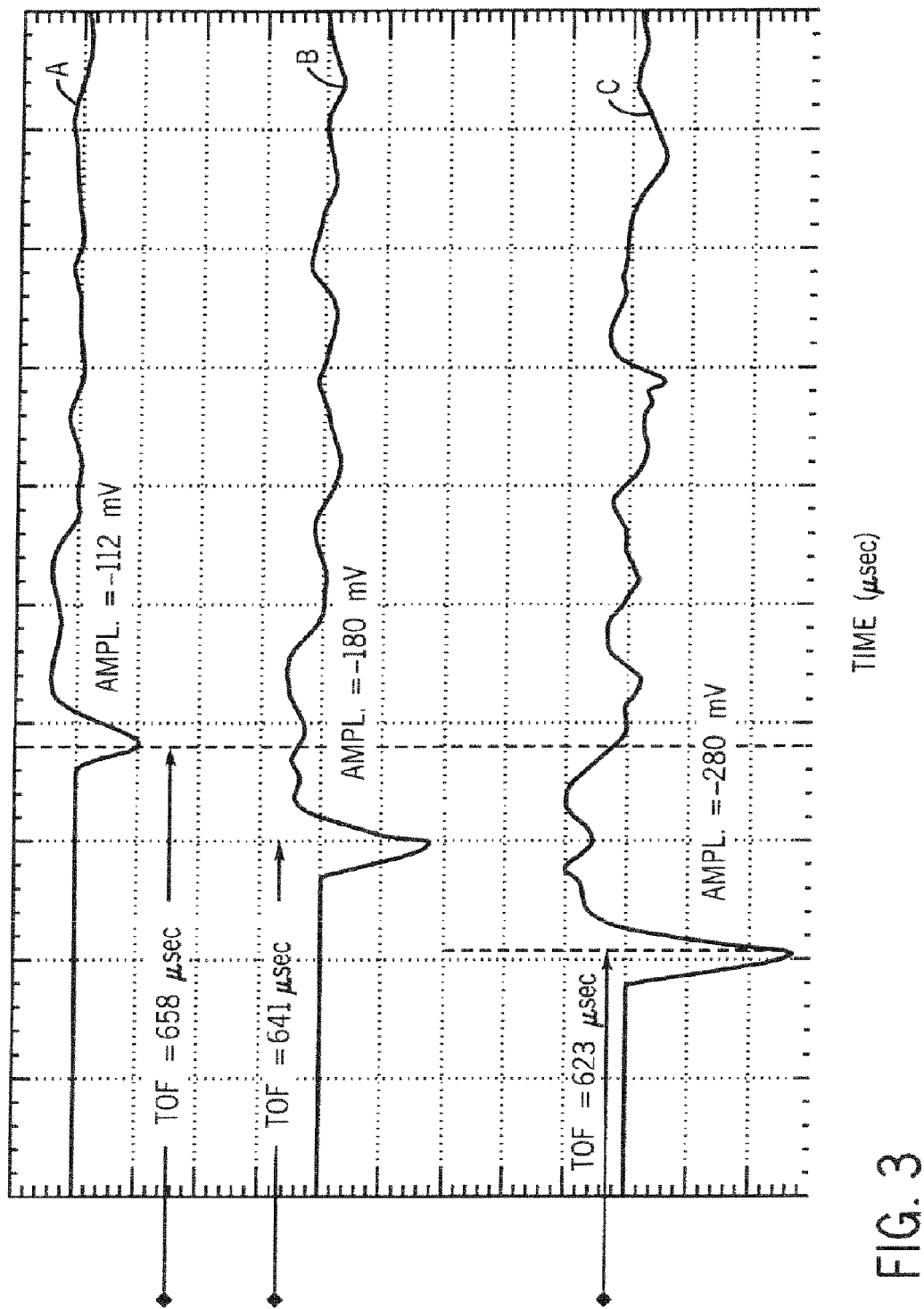
FIG. 3 is a graphical comparison of several residual energy amplitudes and time-of-flights for a variety of laser beams having different energy levels.

As shown in FIG. 3, as the energy level of the laser beam is adjusted, the time-of-flight value of the residual energy shockwave can be compared to statistical values associated with desired coupling of the energy of the laser generated shock wave with a workpiece. Such an association provides an indication that an acceptable peen has been produced as determined by the time-of-flight value of the residual energy signal. Plot A in FIG. 3 is indicative of a 1.27 Joule per pulse laser beam impinged on a workpiece. After impingement of the laser beam on a workpiece, a time-of-flight of approximately 658.5 microseconds is determined with a signature amplitude of approximately −112 millivolts. When the energy level of the laser source is increased to 2.03 Joules per pulse as shown in plot B, a faster and higher amplitude signal are perceived from the laser shock event. That is, a time-of-flight of the laser shock event of approximately 641 microseconds is associated with an amplitude of approximately −180 millivolts. As shown in plot C, as the energy of the laser beam is increased to 3.51 Joules per pulse, a time-of-flight value of 623.1 microseconds is recognized with an amplitude of −280 millivolts. Understandably, these energy levels are merely exemplary and other energy levels of the laser source may be utilized to generate a peen event.

As previously discussed with respect to FIG. 2, as the quality of the coupling of the energy of the laser beam with the part increases, the time required for the residual energy or shockwave to travel from the shock location to sensor 14 decreases. That is, more of the energy of the laser pulse has been coupled into the shockwave to be utilized to produce a peen in the part. There are several events that can reduce the coupling efficiency of the laser pulse energy into the shockwave without changing the pulse energy. These events can include, for example, damaged beam delivery optics, obstruction of a beam delivery path, and/or interruption/disruption of the containment layer. Referring back to FIG. 3, a particular peen pulse with a sensed amplitude that is shifted to the right as compared to the comparable powered laser pulse represented by plots A-C, indicates that it took more time than preferred for the residual energy of that particular pulse to reach the sensor. That is, the residual energy was traveling slower than a desired time-of-flight and indicates that an insufficient coupling has occurred and therefore, an unsatisfactory peen has been produced. Understandably, there will be a time-of-flight tolerance range associated with a respective part being processed at a respective laser power level wherein any time-of-flight values within this control range indicate production of acceptable peens. Likewise, for a part that includes many peens, there may be a control limit to define a tolerable number of unsatisfactory peen events. Such a control limit would allow processing of the part until the number of unacceptable peens is produced and at which time the part can be rejected. Such a system allows for repetitive processing of a plurality of parts, on-the-fly control and adjustment of the peening system, real-time individual peen quality monitoring, and non-destructive quality control of the parts being processed.

Therefore, in accordance with one embodiment of the present invention, a controller includes an input and a processor. The input is configured to receive a signal from a transducer that is indicative of a laser shock event at a workpiece. The processor is connected to the input and is configured to determine a travel time from the workpiece to the transducer of energy associated with the laser shock event and output a determination of peen quality from the travel time.

Another embodiment of the present invention includes a laser shock peening system having a laser source, a sensor, and a controller. The laser source is constructed to emit a laser beam at a workpiece and the sensor is directed toward the workpiece to detect generation of a shock event thereat. The controller is connected to the laser source and the sensor and is configured to receive a first signal from the laser source and a second signal from the sensor. The controller is further configured to determine a time-of-flight value from the first signal and the second signal, and determine a quality of a peen from the time-of-flight value.

A further embodiment of the present invention includes a method of monitoring a laser shock peening process which detects emission of a laser beam from a laser source towards a workpiece for initiation of a peen event, detects a residual energy associated with generation of a shockwave generated by impingement of the laser beam on an absorption layer, determines a time duration between generation of the residual energy and detection of the residual energy, and derives peen quality from the determined time duration.

The present invention has been described in terms of the preferred embodiment, and it is recognized that equivalents, alternatives, and modifications, aside from those expressly stated, are possible and within the scope of the appending claims.

What is claimed is:

1. A controller comprising:
   a first input configured to receive a signal transmitted from a transducer indicative of at least one of spectral data and amplitude data of energy associated with a laser shock event at a workpiece in response to a laser beam generated via a laser source;
   a second input configured to receive a signal from the laser source; and
   a processor connected to the first and second inputs and configured to determine a travel time of energy associated with the laser shock event from the workpiece to the transducer, the travel time based on the energy of the laser beam generated via the laser source as derived from the first and second input signals, and output a determination of peen quality based on the travel time in response thereto.

2. The controller of claim 1 wherein the laser source is a Q-switched laser.

3. The controller of claim 1 further configured to control a distribution of a containment material.

4. The controller of claim 3 wherein the distribution of the containment material is further defined as an amount and a direction of a water flow.

5. A laser shock peening system comprising:
   a laser source constructed to emit a laser beam at a workpiece;
   a sensor directed toward the workpiece to detect a shock event; and
   a controller connected to the laser source and the sensor, the controller configured to:
   (A) receive a first signal from the laser source and a second signal from the sensor;
   (B) determine a travel time of energy of the laser beam generated via the laser source, the travel time based on the energy of the laser beam generated via the laser source as derived from the first and second input signals; and
   (C) determine a quality of a peen from the travel time of energy value.

6. The laser shock peening system of claim 5 further comprising an amplifier disposed between the sensor and the controller and configured to condition the signal received from the sensor.

7. The laser shock peening system of claim 5 further comprising a filter disposed between the sensor and the controller and configured to condition the signal received from the sensor.

8. The laser shock peening system of claim 5 wherein the quality of a peen is determined during real-time operation of the system.

9. The laser shock peening system of claim 5 further comprising an electronic database configured to associate a quality of a peen with an average peen of a number of peens and a part of a number of parts.

10. The laser shock peening system of claim 5 wherein the controller is constructed to generate an alert when a determined quality of a peen is beyond a threshold.

11. The laser shock peening system of claim 10 wherein the controller is configured to suspend operation of the laser source for a subsequent emission of a laser beam when an alert has been generated.

12. The laser shock peening system of claim 5 wherein the controller is configured to control operation of a positioning system, the positioning system constructed to orient the laser source and the workpiece such that the laser beam impinges the workpiece at a desired location and a desired inclination.

13. The laser shock peening system of claim 5 wherein the sensor is positioned at least 30 mm from the workpiece.

14. A method of monitoring a laser shock peening process comprising the steps of:
    (A) detecting emission of a laser beam from a laser source towards a workpiece for initiation of a peen event;
    (B) detecting a residual energy associated with generation of a shockwave generated by impingement of the laser beam on an absorption layer;
    (C) determining a time duration between generation of the residual energy and detection of the residual energy, the time duration based on the energy of the laser beam as derived from the detected emission and the detected residual energy; and
    (D) deriving peen quality from the determined time duration.

15. The method of claim 14 further comprising the step of repeating steps (A) through (D) for each of a plurality of peen events.

16. The method of claim 15 further comprising the step of determining a part quality from the plurality of derived peen qualities.

17. The method of claim 14 further comprising the step of providing an alert when a derived peen quality is unacceptable.

18. The method of claim 17 further comprising the step of suspending laser beam emission for a subsequent peen event upon determination of an unacceptable peen quality for a previous peen event.

19. The method of claim 14 further comprising the step of automatically adjusting at least one of a laser beam emission parameter and a peen event parameter for a subsequent peen event if a preceding peen event is deemed unacceptable.

20. The method of claim 19 wherein the step of automatically adjusting the parameter achieves an acceptable determined time duration for the subsequent peen event.

* * * * *